United States Patent [19]

Willms et al.

[11] 4,448,731

[45] May 15, 1984

[54] 1,2-DIHALOGENOALKYLSULFONYL ISOCYANATES AND 1,2-DI-HALOGENOCYCLOALKYLSULFO-NYL ISOCYANATES AND PROCESS FOR THEIR MANUFACTURE

[75] Inventors: Lothar Willms, Unkel; Dieter Günther; Thomas Hüttelmaier, both of Kelkheim, both of Fed. Rep. of Germany

[73] Assignee: Hoechst Aktiengesellschaft, Frankfurt, Fed. Rep. of Germany

[21] Appl. No.: 412,848

[22] Filed: Aug. 30, 1982

[30] Foreign Application Priority Data

Sep. 1, 1981 [DE] Fed. Rep. of Germany ....... 3134548

[51] Int. Cl.$^3$ .......................................... C07C 143/828
[52] U.S. Cl. ......................... 260/545 R; 204/158 HA
[58] Field of Search ............. 260/545 R; 204/158 HA

[56] References Cited

U.S. PATENT DOCUMENTS 4,375,436 3/1983 Wegener et al. ............... 260/545 R

FOREIGN PATENT DOCUMENTS 1226565 10/1966 Fed. Rep. of Germany .
1230016 12/1966 Fed. Rep. of Germany .

OTHER PUBLICATIONS

Günther et al, Chem. Ber., vol. 103, pp. 663–669, (1970).

*Primary Examiner*—Dolph H. Torrence
*Attorney, Agent, or Firm*—Curtis, Morris & Safford

[57] ABSTRACT

Compounds of the formula

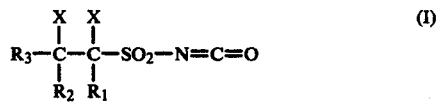

wherein X is halogen, $R_1$ and $R_2$ are hydrogen, halogen, (halo)alk(en)yl, (halo)alkoxyalkyl or together form an (optionally substituted) alkylene bridge, and $R_3$ is hydrogen, alkyl or halogen are valuable intermediates in particular for the manufacture of pesticides.

4 Claims, No Drawings

1,2-DIHALOGENOALKYLSULFONYL ISOCYANATES AND 1,2-DI-HALOGENOCYCLOALKYLSULFONYL ISOCYANATES AND PROCESS FOR THEIR MANUFACTURE

The present invention relates to new 1,2-dihalogenoalkylsulfonyl isocyanates and 1,2-dihalogenocycloalkylsulfonyl isocyanates of the formula

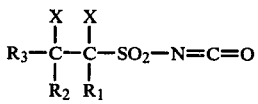

wherein $R_1$ and $R_2$, independent of each other, are hydrogen, halogen, ($C_1$–$C_4$)alkoxy, saturated or unsaturated, branched or linear $C_1$–$C_6$ alkyl optionally substituted by up to 4 halogen atoms, and optionally interrupted by an oxygen atom or $R_1$ and $R_2$, together with both adjacent carbon atoms, may form a 5- to 7-membered alicyclic ring optionally unsaturated and/or substituted by 1 to 3 halogen atoms or by 1 to 2 ($C_1$–$C_3$) alkyl groups, $R_1$ and $R_2$ having optionally together up to 11 carbon atoms, $R_3$ is hydrogen, halogen or ($C_1$–$C_4$)alkyl and X is halogen.

Owing to their reactivity, the compounds according to the invention are interesting intermediates, for example for the preparation of plant protection agents, pharmaceuticals or textile auxiliaries.

It is known to add chlorosulfonyl isocyanate to unsaturated hydrocarbons to obtain 2-chloroalkyl- or 2-chlorocycloalkylsulfonyl isocyanates or 3-oxo-2-[2-chloroalkyl]-isothiazolidine-1,1-dioxides in the presence of free radical-forming agents, depending on the reaction conditions applied [cf. Chem. Ber. 103, 663 (1970); German Auslegeschriften Nos. 1,211,165 and 1,226,565].

The preparation of 1-halogeno-2-chloroalkyl- or -cycloalkylsulfonyl isocyanates according to the aforementioned process is not possible. The addition of chlorosulfonyl isocyanate to vinyl chloride initiated by free radicals leads to 2,2-dichloroethylsulfonyl isocyanate, 2,4,4-trichlorobutylsulfonyl isocyanate and 2,4,6,6-tetrachlorohexylsulfonyl isocyanate and not to 1,2-dichloroethylsulfonyl isocyanate (cf. German Ausleges-chrift No. 1,226,565).

The desired compounds are obtained in very simple manner by reacting 1,2-unsaturated alkenyl- or cycloalkenylsulfonyl isocyanates of formula II

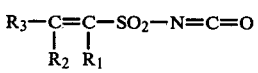

with halogen.

This process is preferable used for the preparation of 1,2-dichloro- or 1,2-dibromoalkylsulfonyl isocyanates and 1,2-dichloro- or 1,2-dibromocycloalkylsulfonyl isocyanates.

Depending on the type of the substituents $R_1$, $R_2$ and $R_3$ and on the configuration of the unsaturated compounds used, the halogen addition may possibly furnish diastereomeric compounds, which may be obtained in a pure state in some cases, for example by fractional distillation (cf. for example Example 2).

Examples of compounds to be prepared by the process of the present invention are listed hereinafter:

1,2-dibromomethylsulfonyl isocyanate (B.p. 74° C./6.7 Pa);

1,2,2-trichloroethylsulfonyl isocyanate (B.p. 60° C./8 Pa);

threo-1,2-dibromopropylsulfonyl isocyanate (B.p. 74° C./6.7 Pa);

1,2,3-trichloropropylsulfonyl isocyanate;

1,2-dichloro-3-methoxypropylsulfonyl isocyanate;

1,2-dichloro-1-methylpropylsulfonyl isocyanate (B.p. 42° C./1.33 Pa);

1,2-dibromo-1-methylpropylsulfonyl isocyanate (B.p. 62° C./4 Pa);

1,1,2-trichloropropylsulfonyl isocyanate;

1,2-dibromo-4,4-dichlorobutylsulfonyl isocyanate;

1,2-dibromopentylsulfonyl isocyanate;

1,2-dibromohexylsulfonyl isocyanate;

1,2,3-trichloro-2-methylpropylsulfonyl isocyanate;

1,2-dichloro-1-chloromethylpropylsulfonyl isocyanate;

1,2-dibromocyclohexylsulfonyl isocyanate (B.p. 110° C./133 Pa);

1,2,6-trichlorocyclohexylsulfonyl isocyanate.

Suitable starting compounds for the process according to the present invention are, for example, vinylsulfonyl isocyanate, 2-chlorovinylsulfonyl isocyanate, propenylsulfonyl isocyanate, 3-chloropropenylsulfonyl isocyanate, 1-methylpropenylsulfonyl isocyanate, butenyl-1-sulfonyl isocyanate, 4-chlorobutadienylsulfonyl isocyanate, 4,4-dichlorobutenyl-1-sulfonyl isocyanate or cyclohexenyl-1-sulfonyl isocyanate. Said alkenyl- and cycloalkylsulfonyl isocyanates, respectively, unsaturated in the 1,2 position, can be readily prepared from the corresponding 2-chloroalkyl- and cycloalkylsulfonyl isocyanates, respectively, by splitting off hydrogen chloride (cf. German Auslegeschriften Nos. 1,230,016 and 1,568,640).

The process may be carried out in the following manner: The alkenyl- and cycloalkenylsulfonyl isocyanates, respectively, unsaturated in the 1,2 position, are reacted with the corresponding halogen, while thoroughly mixing, preferably in the presence of inert solvents or diluents and of free radical-forming initiators. Suitable solvents or diluents are, for example, benzene, toluene, heptane, carbon tetrachloride, chloroform, dichloromethane, 1,1,2-trichloroethane and mixtures thereof. Suitable free radical-forming initiators (catalysts) are compounds capable of forming free radicals under the reaction conditions applied, for example peroxides or azo compounds. Examples hereof are azo-bis-isobutyronitrile, diisopropyl peroxidicarbonate, acetylcyclohexanesulfonyl peroxide, di-tert.butyl peroxide and benzoyl peroxide. The catalyst may be used in an amount from 0.01 to 20 weight %, preferably of from 0.01 to 5 weight %, referred to the sulfonyl isocyanate used as starting compound. The free radicals may be produced moreover by irradiation of the reaction mixtures, for example with UV light.

The molar ratio of the reaction components is not critical and may vary within wide limits. Any alkenyl- or cycloalkenylsulfonyl isocyanate, respectively, unsaturated in the 1,2 position, used in excess, may be recovered during working up, for example by distillation.

Molar ratios of sulfonyl isocyanate to halogen of from 0.8:1 to 1:4, in particular of from 1:1 to 1:3 are preferred for economic reasons. Further unsaturated groups optionally present in the aliphatic or cycloaliphatic radical of the 1,2-unsaturated alkenyl- and cycloalkenylsulfonyl isocyanates are likewise halogenated, if an excess of halogen has been used, depending on the reaction conditions applied.

The reaction temperature may vary within wide limits. A temperature of from about −60° C. to 140° C., preferably of from −10° to 80° C., is chosen for practical reasons.

The reaction time may vary with the conditions under which the process of the invention is carried out. It is generally from 1 to 48 hours.

The reaction is carried out usually under normal pressure. Elevated pressure, for example a pressure of from 1 to 1,000 atmospheres, may be applied alternatively.

The halogen current may be diluted optionally by admixing inert gases, for example nitrogen or argon.

The compounds according to the invention are new reactive substances suitable for use as intermediates for plant protection agents, pharmaceuticals and textile auxiliaries and as intermediates for a great number of further reactions. For example, they may be reacted with heterocyclic amines, which is a new simplified method for the manufacture of alkyl- and cycloalkylsulfonyl ureas in a high yield, the latter having excellent herbicidal properties (cf. German patent application Nos. P 3,111,451.2 and P 3,131,489.9). Surprisingly an exchange of the α-halogen atom is not observed during this reaction even if an excess of amine has been used, as reported, for example, on analogous halogenoalkyl isocyanates (cf. J. org. Chem. 28, 1830 (1963)).

The following examples serve to illustrate the process for the manufacture of the compounds according to the invention:

EXAMPLE 1

399 g (3 mols) of vinylsulfonyl isocyanate are gassed with chlorine in 1.2 l of dichloromethane while irradiating with an ultraviolet high pressure immersion lamp. The inner temperature is kept between 20° and 30° C. by cooling. The chlorine absorption is complete after 1 hour (consumption about 215 g) and the reaction mixture is freed from solvent on a rotary evaporator. The residue is subjected to a thin layer distillation at 100° C./26.6 Pascal leaving 368 g (1.8 mols; 60% of the theory) of 1,2-dichloroethylsulfonyl isocyanate. A second distillation in a Vigreux column yields a product having a melting point of 43° C./7.98 Pascal.

Analysis: 1,2-Dichloroethylsulfonyl isocyanate $C_3H_3Cl_2NO_3S$ (molecular weight 204.05): calc.: C: 17.7, H: 1.5, Cl: 34.8, N: 6.9, S: 15.7%; found: C: 17.8, H: 1.9, Cl: 34.2, N: 7.0, S: 16.0%.

EXAMPLE 2

200 g (1.36 mols) of propenylsulfonyl isocyanate are dissolved in 0.8 g of dichloromethane and the solution obtained is chlorinated upon addition of 1 ml of a diisopropyl peroxidicarbonate solution (40% solution in phthalate). The temperature is kept between 25° to 35° C. by cooling. After 4 hours, the reaction mixture has absorbed about 120 g of chlorine. The solvent is separated by distillation and the residue is subjected to a thin layer distillation at 60° C./7.98 Pascal. 272 g of a crude product which may be split up into two products by fractionating distillation are obtained:

164 g of threo-1,2-dichloropropylsulfonyl isocyanate, B.p. 42°-43° C./1.33 Pascal (0.75 mol, 56% of the theory); 80 g erythro-1,2-dichloropropylsulfonyl isocyanate, B.p. 55° C./1.33 Pascal (0.37 mol, 27.2% of the theory).

Analysis: threo-1,2-dichloropropylsulfonyl isocyanate $C_4H_5Cl_2NO_3S$ (molecular weight 218.07): calc.: C: 22.0, H: 2.3, Cl: 32.5, N: 6.4, S: 14.7%; found: C: 22.4, H: 2.3, Cl: 31.5, N: 6.6, S: 14.7%.

erythro-1,2-dichloropropylsulfonyl isocyanate $C_4H_5Cl_2NO_3S$ (molecular weight 218.07): found: C: 22.4, H: 2.3, Cl: 32.3%.

EXAMPLE 3

38.6 g (0.2 mol) of 4-chlorobutadienylsulfonyl isocyanate are dissolved in 100 ml of chloroform and 64 g (0.4 mol) of bromine in 100 ml of chloroform are added to the resultant solution at room temperature within 1 hour. The batch is stirred for 1 hour at room temperature and for 9 hours at 60° C. Separation of the solvent by distillation gives 68.9 g (67% of the theory) of 1,2,3,4-tetrabromo-4-chlorobutylsulfonyl isocyanate in the form of a yellowish oil which decomposes during distillation (refraction index $n_D^{20}$: 1.5698.

EXAMPLE 4

100 g (0.53 mol) of cyclohexenyl-1-sulfonyl isocyanate are chlorinated in the manner described in Example 1 in dichloromethane at a temperature of from −10° to 0° C. Distillative working up gives 54.6 g (0.21 mol, 40% of the theory) of 1,2-dichlorocyclohexylsulfonyl isocyanate having a boiling point of 100° C./6.65 Pascal.

Analysis: 1,2-Dichlorocyclohexylsulfonyl isocyanate $C_7H_9Cl_2NO_3S$ (molecular weight 258.12): calc.: C: 32.6, H: 3.5, Cl: 27.5, S: 12.4%; found: C: 32.4, H: 3.6, Cl: 26.5, S: 12.5%.

What is claimed is:

1. A compound of the formula

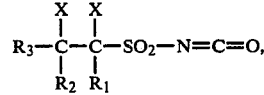

wherein
X is halogen;
$R_3$ is hydrogen, halogen, or $C_1$–$C_4$ alkyl;
$R_1$ and $R_2$, taken alone, are the same or different and are hydrogen, halogen, ($C_1$–$C_4$) alkoxy, ($C_1$–$C_6$) alkyl, such alkyl substituted with up to 4 halogen atoms, or such alkyl interrupted by an oxygen atom; or
$R_1$ and $R_2$, taken together with the carbon atoms to which the are attached, form a 5- to 7-membered saturated or unsaturated alicycle or such an alicycle substituted by 1 to 3 halogen atoms or mono- or di-substituted by ($C_1$–$C_3$) alkyl.

2. A compound as in claim 1 wherein $R_1$ and $R_2$ are the same or different and are hydrogen, chlorine, bromine, ($C_1$–$C_4$) alkyl, ($C_1$–$C_2$) halogenoalkyl, or methoxymethyl.

3. A compound as in claim 1 wherein $R_1$ and $R_2$ taken together, are trimethylene or tetramethylene.

4. The method of making a compound as in claim 1 which comprises halogenating a compound of the formula

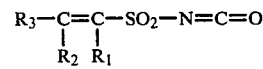

at a temperature from −60° C. to 140° C. in the presence of free radicals generated by a radical-forming initiator or by irradiation of the reagents.

* * * * *